United States Patent [19]

Gregory

[11] 4,306,552
[45] Dec. 22, 1981

[54] PLASTICIZED POLY-ε-CAPROLACTONE FILM

[75] Inventor: John B. Gregory, Wayland, Mass.

[73] Assignee: The United States of America as represented by the Secretary of the Navy, Washington, D.C.

[21] Appl. No.: 177,169

[22] Filed: Aug. 12, 1980

[51] Int. Cl.³ .............................................. A61L 15/00
[52] U.S. Cl. .................................................... 128/156
[58] Field of Search .............................. 128/155–156, 128/335.5

[56] References Cited

U.S. PATENT DOCUMENTS

| | | |
|---|---|---|
| 2,371,001 | 3/1945 | Stone . |
| 3,903,882 | 9/1975 | Augurt ................................. 128/155 |
| 3,935,308 | 1/1976 | Wise et al. . |
| 3,949,742 | 4/1976 | Nowakowski ....................... 128/156 |
| 4,060,081 | 11/1977 | Yannas et al. ........................ 128/156 |
| 4,215,686 | 8/1980 | Gregory et al. ..................... 128/156 |

Primary Examiner—C. Fred Rosenbaum
Attorney, Agent, or Firm—Robert F. Beers; W. Thom Skeer

[57] ABSTRACT

A wound dressing for burn patients comprises a two layer compress made of poly-ε-caprolactone material. One layer is configured for optimum wound contact while the other is configured for moisture control.

23 Claims, 3 Drawing Figures

PLASTICIZED POLY-ε-CAPROLACTONE FILM

BACKGROUND OF THE INVENTION

1. Field of the Invention

The invention relates to the fields of medicine and organic chemical engineering. More particularly, the invention relates to the manufacture of healing promoting wound dressings. By way of further characterization, the invention pertains to a moisture control burn wound dressing used in instances where skin growth is necessary. More particularly, but without limitation thereto, the invention will be disclosed as it relates to a laminated article to serve as artificial skin during the treatment and healing of skin damaging burns.

2. Description of the Prior Art

A burn covering has two functions. First, it should prevent excessive loss of body fluids and proteins due to uncontrolled evaporative water loss from the burned area. This water loss can be of the order of ten times greater than the normal rate of evaporation through the skin. For a victim with severe burns over a large portion of his body, the total loss is substantial and can lead to shock and death during the immediate (0-5 days) post-burn period. Second, it should promote the formation of a viable interface between the wound and covering.

A viable interface is defined as a living, growing fibrin network and is desirable for two reasons. One, neutrophils and macrophages readily enter the network and kill bacteria. This action helps not only to prevent burn wound sepsis—a major cause of limb loss or death—but also to remove exudate which is typically found in a wound. Two, once the fibrin network is developed, the damaged area will more readily accept an autograft—the ultimate goal of burn therapy. A viable interface is indicated by adherence of the covering to the wound. The covering must be flexible in order to conform to the contours of the body so adherence is complete.

Presently, human-donor and porcine skin are the most successful and widely used burn coverings. Both promote the formation of a viable interface and control the evaporative water loss from the burn area. Coverings composed of those skins must be removed or are rejected by the body every three to five days. New skins are then applied. Collagen film has also been tested as an artificial skin.

Laminates of synthetic, non-biodegradable materials are also available for burn treatment. Silastic film laminated with nylon velour has been applied to animals. For example, fabrics impregnated with latex and commercially available synthetic plastic compositions have been used. Metallic foils have also been used as backing material for these types of wound dressings. Although satisfactory for limited purposes and applications, the known burn dressings lack one or more optimum parameters for burn treatment applications where skin growth is an important factor.

It is also known in the art to spray the burned portion of the patient with a solution of poly-ε-caprolactone in a solvent which evaporates to leave a covering layer. Such a treatment, although practical for emergency treatment of flash burn victims, lacks the advantages of compress type treatment in promoting the growth of new skin.

SUMMARY OF THE INVENTION

The invention relates to a dressing useful in treatment of burns using a plasticized poly-ε-caprolactone vapor control and support layer bonded to a porous layer of the same material formed from a foam, a flocked fabric, or a velvet. The porous layer configures to promote new skin growth.

Accordingly, it is an object of the invention to provide a lamination useful in treatment of wounds.

Another object of the invention is the provision of a laminate which is biodegradable.

A further object of the invention is the provision of a wound dressing which promotes the growth of skin over a wound.

These and other objects of the invention will become clear in considering the following description, claims, and drawings.

DESCRIPTION OF THE PREFERRED EMBODIMENT

Figure 1:
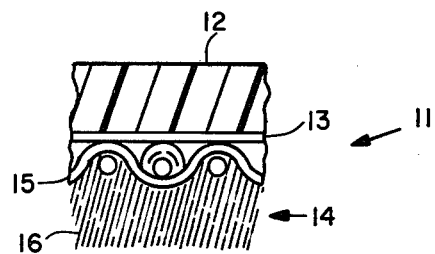
FIG. 1 is a sectional view of a form of the invention employing a velvet contact layer.

Referring to FIG. 1, the wound dressing of the invention is indicated generally at 11. A layer of plasticized poly-ε-caprolactone 12 provides a body conforming support for the laminate and is configured as a sheet to control moisture transmission therethrough. Layer 12 is from 0.001 to 0.01 inches in thickness and the poly-ε-caprolactone has a molecular weight between 2,000 and 300,000. The material thus formed has the advantage of permitting sufficient moisture flow to prevent the collection of excess amounts of body fluid thereunder and yet prevent dehydration of the wound area. A layer 14 is bonded to layer 12 at a junction 13. This bonding is accomplished by taking the film 12 and moistening it with a suitable solvent and pressing the layer 14 thereagainst. The softening provided by the solvent interacts with both layers 14 and 12 to permit a welding or joining along the contacting surface.

The layer 14 which contacts the wound area where it is desirable to promote the growth of skin is, in the illustrated arrangement, made of a plush or velvet material having a woven backing 15 and a contained fibrous nap 16. Both the woven back 15 and the plush 16 are made of the same poly-ε-caprolactone as is backing sheet 12. This dressing has proven to be more comfortable for patients than the silastic-nylon velours of the prior art and have not exhibited failure of the bonding lamination as was common with other known arrangements.

Both the plush and backing sheets may be plasticized by using triacetin or triethylcitrate, or mixtures thereof. These plasticizers prevent hardening of the two layers and permit easy applications and body conforming contact of the laminate. These plasticizing materials are the triacetic acid ester of glycerol and the triester of ethyl alcohol and citric acid, respectively. The hydrolysis products of these esters are ingredients which are found in living organisms and are considered to be biocompatible. Additionally, these particular plasticizers make the laminate more conformable without lowering the watering permeability of the structure beyond the desired range.

The cut plush nap 16 of the arrangement shown in FIG. 1 is particularly easy to remove from the wound without tearing newly formed tissue in comparison to the velours and plushes used heretofor.

For certain burn applications and various parts of the body where the growth of skin is different, other configurations of the invention may be substituted for the embodiment illustrated in FIG. 1.

Figure 2:
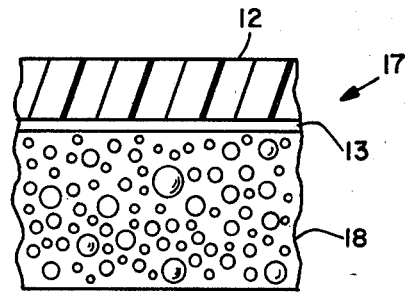
FIG. 2 is a sectional view of the invention employing a foam contact layer.
Figure 3:
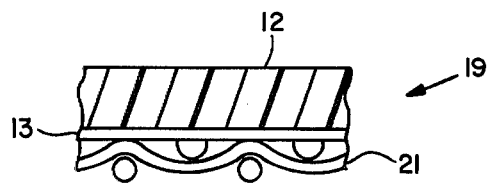
FIG. 3 is a sectional view of the invention employing a fabric contact layer.

Referring to FIG. 2, an alternate form of the invention is illustrated wherein a foam layer 18 is substituted for the velvet plush layer 14 and bonded to layer 12. The same bonding technique used for the species of FIG. 1 may be employed in this arrangement.

Likewise, in some instances, a knit or woven fabric made of poly-ϵ-caprolactone may be employed. In this instance a layer of such fabric indicated at 21 is bonded to the backing 12 to produce the illustrated laminate shown at 19.

In production a polished surface such as stainless steel is used to receive a layer of poly-ϵ-caprolactone in solvent solution thereon and it is allowed to form a solid film of the desired thickness by allowing the solvent to evaporate. A suitable solvent such as acetone is spread over this layer and the layer 14 or the sponge 18 or the fabric 21 is then impressed on the backing film 12 and held in contact therewith to promote the bonding therebetween. This bond has proven to be adequate in test applications and no instances of layer separation has been noted.

The foregoing description taken together with the appended claims constitutes a disclosure such as to enable a person skilled in the biochemical arts and having the benefits of the teachings contained therein to make and use the invention. Further, the structure herein described meets the aforegoing objects of the invention, and generally constitutes a meritorious advance in the art.

What is claimed is:

1. A laminate for wound dressing including a first layer of structural poly-ϵ-caprolactone for contacting living tissue; and
   a second layer of a poly-ϵ-caprolactone film bonded to said first layer for support thereof and control of flow of fluids therethrough and including a plasticizer to ensure a predetermined flexibility for permitting conformation to patient body contours.

2. A laminate according to claim 1 wherein said plasticizer is triacetin.

3. A laminate according to claim 1 wherein said plasticizer is triethylcitrate.

4. A laminate according to claim 1 wherein said plasticizer is a mixture of triethylcitrate and triacetin.

5. A laminate according to claim 1 wherein said first layer is configured to provide a predetermined contact for promoting skin growth at the junction of contact with the patient.

6. A laminate according to claim 5 wherein said first layer is configured as a velvet material.

7. A laminate according to claim 5 wherein said first layer is configured as a foam.

8. A laminate according to claim 5 wherein said first layer is configured as a knitted fabric.

9. A laminate according to claim 1 wherein said first and second layers are bonded by a self-welding of the two layers.

10. A laminate according to claim 2 wherein said first layer is configured as a velvet material.

11. A laminate according to claim 3 wherein said first layer is configured as a velvet material.

12. A laminate according to claim 4 wherein said first layer is configured as a velvet material.

13. A laminate according to claim 2 wherein said first layer is configured as a foam.

14. A laminate according to claim 3 wherein said first layer is configured as a foam.

15. A laminate according to claim 4 wherein said first layer is configured as a foam.

16. A laminate according to claim 2 wherein said first layer is configured as a knitted fabric.

17. A laminate according to claim 3 wherein said first layer is configured as a knitted fabric.

18. A laminate according to claim 4 wherein said first layer is configured as a knitted fabric.

19. A laminate according to claim 2 wherein said first layer is a cut plush.

20. A laminate according to claim 3 wherein said first layer is a cut plush.

21. A laminate according to claim 4 wherein said first layer is a cut plush.

22. A laminate according to claim 5 wherein said first layer is a cut plush.

23. A laminate for the promotion of skin growth comprising:
   a first layer configured to contact a body portion of a patient and to promote the growth of skin and formed of a plasticized layer of poly-ϵ-caprolactone; and
   a second layer of plasticized poly-ϵ-caprolactone self welded to said first layer and configured for supporting said layer in conformation to the body portion of said patient contacted thereby and for controlling the fluid flow therethrough.

* * * * *